(12) United States Patent
Trigg et al.

(10) Patent No.: US 6,913,761 B1
(45) Date of Patent: Jul. 5, 2005

(54) BIOIMPLANT FORMULATION

(75) Inventors: Timothy Elliot Trigg, Warrawee (AU); John Desmond Walsh, Curl Curl (AU); Deborah Ann Rathjen, Thornleigh (AU)

(73) Assignee: Peptech Limited, New South Wales (AU)

( * ) Notice: Subject to any disclaimer, the term of this patent is extended or adjusted under 35 U.S.C. 154(b) by 0 days.

(21) Appl. No.: 09/743,059

(22) PCT Filed: Jul. 20, 1999

(86) PCT No.: PCT/AU99/00585

§ 371 (c)(1),
(2), (4) Date: Jan. 4, 2001

(87) PCT Pub. No.: WO00/04897

PCT Pub. Date: Feb. 3, 2000

(30) Foreign Application Priority Data

| Jul. 20, 1998 | (AU) | ............................................. | PP4730 |
| Jul. 20, 1998 | (AU) | ............................................. | PP4731 |
| May 13, 1999 | (AU) | ............................................. | PQ0324 |

(51) Int. Cl.$^7$ .......................... A61F 2/02; A61K 38/20; A61K 31/21; A61K 38/04

(52) U.S. Cl. ........................ 424/423; 424/450; 514/12; 514/14; 514/15; 514/16; 514/17; 514/18; 514/19; 514/513; 514/515; 530/328

(58) Field of Search .................................. 424/423, 450; 514/12, 14, 15, 16, 17, 18, 19, 513, 514, 515; 530/328

(56) References Cited

U.S. PATENT DOCUMENTS

| 4,578,391 A | 3/1986 | Kawata et al. |
| 6,337,318 B1 * | 1/2002 | Trigg et al. ................... 514/15 |

FOREIGN PATENT DOCUMENTS

| EP | 0 523 330 B1 | 4/1992 |
| EP | 0 523 330 A1 | 1/1993 |
| WO | 94/08623 | 4/1994 |

* cited by examiner

Primary Examiner—Carlos A. Azpuru
(74) Attorney, Agent, or Firm—Nixon & Vanderhye

(57) ABSTRACT

A pharmaceutical and/or veterinary formulation comprising about 2–30% (w/w) (on an active basis) of at least one active agent, about 0.5–20.0% (w/w) of a pore-foaming agent and the balance stearin. Such formulations provided release of the at least one active agent in humans and other animals for periods of 7 days up to about 2 years.

40 Claims, 9 Drawing Sheets

BIOIMPLANT FORMULATION

FIELD OF THE INVENTION

Figure 1:
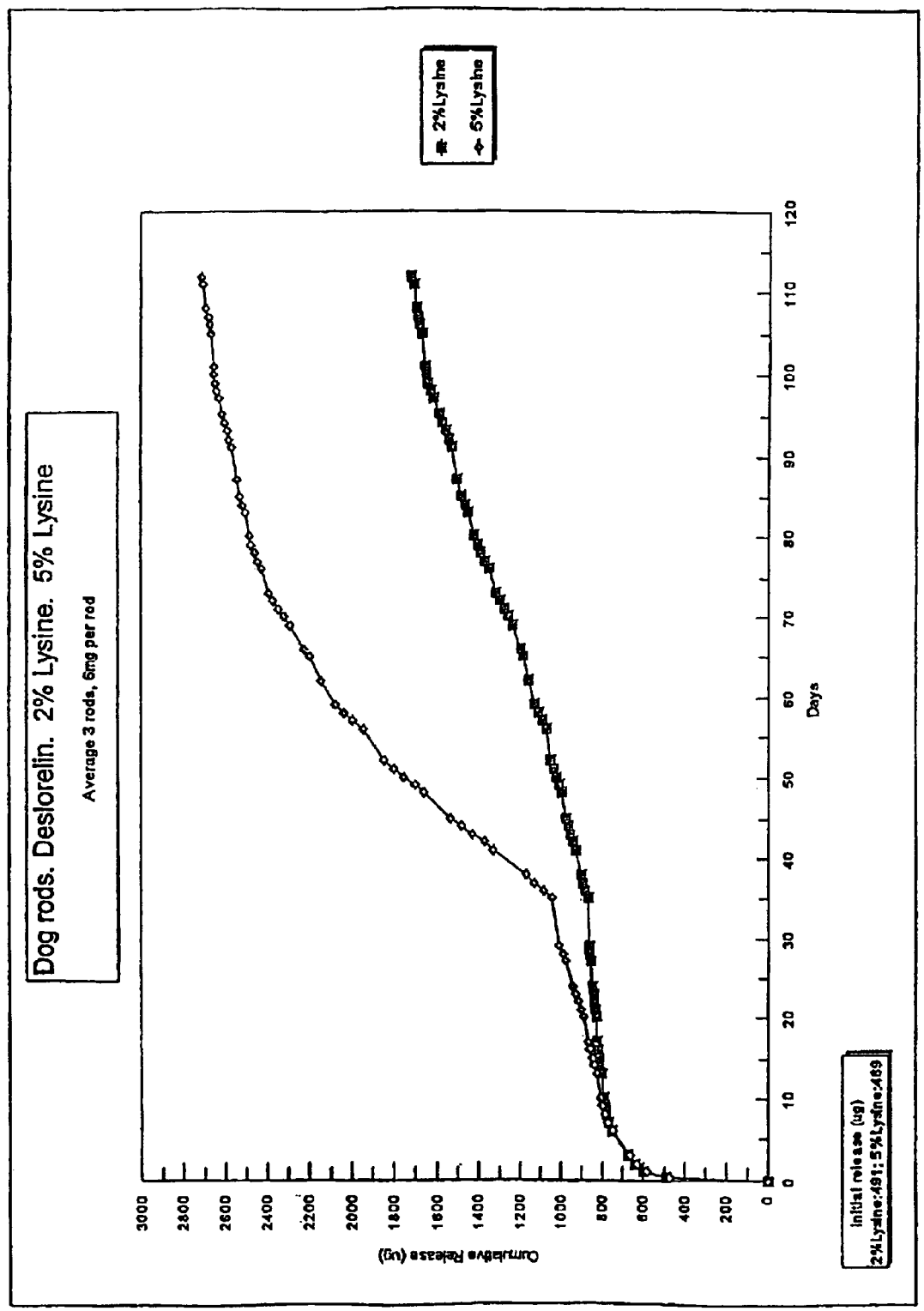

The present invention relates to pharmaceutical and/or veterinary formulations for the sustained release of at least one active agent. Preferred active agents include gonadotropin-releasing hormone (GnRH) agonists (e.g. deslorelin), GnRH antagonists (e.g. cetrorelix), somatostatin analogues (e.g. somatostatin-14 and octreotide), lipid lowering agents (e.g. simvastatin), cyclosporins (e.g. cyclosporin A), angiotensin converting-enzyme inhibitors (e.g. captopril), calcitonins, substance P antagonists, painkillers (e.g. morphine), opioid antagonists (e.g. naltrexone), anti-depressants (e.g. venlafaxine) and non-steroidal anti-inflammatory agents (e.g. naproxen sodium).

BACKGROUND OF THE INVENTION

For reasons including improved efficacy of action and reduced frequency of administration, there is considerable interest in the development of pharmaceutical and veterinary formulations capable of controllably releasing active agents for sustained periods (e.g. up to 6 months or more). Types of pharmaceutical agents that would particularly benefit from the development of such formulations are those which are typically administered by patients themselves over long periods (e.g. insulin for diabetes treatment, and gonadotropin-releasing hormone (GnRH) agonists for reproductive control and treatment of sex hormone-dependent diseases and conditions) and require high levels of patient compliance. In the veterinary context, sustained release formulations would reduce the stress often caused to the animal and veterinarian/owner alike by the need for repeated administration of active agents.

The present applicant's have found that sustained release of at least one active agent in humans and other animals for periods of 7 days up to about 2 years, can be achieved by using a solid formulation comprising stearin as an excipient in combination with a substance which, while not wishing to be bound by theory, appears to form pores and/or cracks in the excipient to enable the release of the active agent(s).

SUMMARY OF THE INVENTION

Thus, in a first aspect, the present invention provides a pharmaceutical and/or veterinary formulation comprising about 2–30% (w/w) (on an active basis) of at least one active agent, about 0.5–20.0% (w/w) of a pore-forming agent and the balance stearin.

In a preferred embodiment, the formulation comprises about 5–10% (w/w) (on an active basis) of at least one active agent, about 1.0–10.0% (w/w) of a pore-forming agent and the balance stearin.

In a more preferred embodiment, the formulation comprises about 5–10% (w/w) (on an active basis) of at least one active agent, about 2.0–5.0% (w/w) of a pore-forming agent and the balance stearin.

In a second aspect, the present invention provides a method of treating a disease or condition in a human or other animal, the method comprising administering to the human or other animal the formulation of the first aspect of the invention.

DETAILED DISCLOSURE OF THE INVENTION

The at least one active agent utilised in the formulation of the present invention, may be selected from agents having pharmaceutical or veterinary significance and may be any or a combination of peptides (e.g. hormones and antigens), polypeptides and proteins, and nucleic acid compounds and derivatives such as DNA and RNA.

Preferred active agents include:

(1) GnRH Agonists

Particularly preferred GnRH peptide agonists are deslorelin (described in U.S. Pat. No. 4,218,439), eulexin (described in FR7923545, WO 86/01105 and PT100899), goserelin (described in U.S. Pat. Nos. 4,100,274, 4,128,638, GB9112859 and GB9112825), leuprolide (described in U.S. Pat. Nos. 4,490,291, 3,972,859, 4,008,209, 4,005,063, DE2509783 and U.S. Pat. No. 4,992,421), dioxalan derivatives such as are described in EP 413209, triptorelin (described in U.S. Pat. Nos. 4,010,125, 4,018,726, 4,024,121, EP 364819 and U.S. Pat. No. 5,258,492), meterelin (described in EP 23004), buserelin (described in U.S. Pat. Nos. 4,003,884, 4,118,463 and 4,275,001), histrelin (described in EP217859), nafarelin (described in U.S. Pat. No. 4,234,571, WO93/15722 and EP52510), lutrelin (described in U.S. Pat. No. 4,089,946), leuprorelin (described in Plosker et al., Drugs 48 930–967, 1994) and LHRH analogues such as are described in EP181236, U.S. Pat. Nos. 4,608,251, 4,656,247, 4,642,332, 4,010,149, 3,992,365 and 4,010,149. The disclosures of each the patent specifications and papers referred to above are incorporated herein by reference.

The most preferred GnRH agonists are goserelin, deslorelin, leuprorelin, triptorelin, meterelin, buserelin, histrelin, nafarelin and combinations thereof. The formulae of these compounds are provided below:

Goserelin $C_{59}H_{64}N_{18}O_{14}C_2H_4O_2$ D-Ser(Bu$^t$)$^6$Azgly$^{10}$-LHRH Acetate 3-[5-oxo-L-prolyl-L-tryptophyl-L-seryl-L-tyrosyl-(3-O-tert-butyl)-D-seryl-L-leucyl-L-arginyl-L-prolyl] cabazamide acetate.

Deslorelin 6-D-tryptophan-9-(N-ethyl-L prolinamide)-10-deglycinamide P Glutamine-Histidine-Tryptophan-Serine-Tyrosine-D Tryptophan-Leucine-Arginine-Proline-ethylamide.

Leuprorelin $C_{59}H_{64}N_{16}O_{12}$, $C_2H_4O_2$ Leuprorelin Acetate 5-oxo-L-prolyl-L-histidyl-L-tryptophyl-L-seryl-L-tyrosyl-D-leucyl-L-arginyl-N-ethyl-L-prolinamide acetate.

Triptorelin $C_{59}H_{64}N_{10}O_{12}$, $C_2H_4O_2$ D-TRp$^6$-LHRH 5-oxo-L-prolyl-L-histidyl-L-tryptophyl-L-seryl-L-tyrosyl-D-tryptophyl-L-leucyl-L-arginyl-L-prolylglycinamide.

Meterelin Des Gly$^{10}$-2-methyl-D-Trp$^6$-Pro-ethyl-amide$^9$ LHRH.

Buserelin $C_{50}H_{66}N_{16}O_{13}$, $C_2H_4O_2$ D-Ser(Bu$^t$)$^6$-Pro9-NEt LHRH Acetate Oxo-L-prolyl-L-histidyl L-tryptophyl-L-seryl-L-tyrosyl-O-tert-butyl-D-seryl-L-leucyl-L-arginyl-N-ethyl-L-prolinamide acetate.

Histrelin Pro-His-Trp-Ser-Tyr-Leu-D(N-benzyl) His-Arg-Pro-N-ethylamide.

Nafarelin $C_{86}H_{63}N_{17}O_{13}$, $xC_2H_4O_2yH_2O$Oxo-L-prolyl-L-histidyl-L-tryptophyl-L-seryl-L-tyrosyl-3-[2-naphthyl]-D-alanyl-L-leucyl-L-arginyl-N-ethyl-L-prolylglycinaminde acetate hydrate.

Formulations according to the invention which include a GnRH agonist as the at least one active agent may be used for controlling reproductive function or for the treatment of any disease or condition wherein reduction of sex hormone (i.e. testosterone or estradiol) levels over a prolonged period is beneficial. Examples include prostrate cancer, ovarian and breast cancer, benign hormone-dependent disorders such as endometriosis, myoma and premenstrual tension, uterine fibroids, induction of eudometrial atrophy prior to surgery, suppression of germ cell activity in chemotherapy, hirsutism, cyclic auditory dysfunction, porphyria and precocious puberty in children, benign prostatic hypertension in dogs and for use in other conditions where castration is known to have a beneficial clinical effect, including restoration of T cell-mediated immunity, (2) GnRH Antagonists Particularly preferred GnRH antagonists are ramorelix (L-prolone,1-(NZ-(N-(N-(N-(N-(N-(N-(N-acetyl-3-(2-naphhthalenyl) -D-alanyl)-4-chloro-D-phenylalanyl)-D-tryptophyl)-L-seryl) -L-tyrosyl-O-(6-deoxy-alpha-L-mannopyranosyl)-D-seryl)-L-leucyl)-L-arginyl)-2-(aminoacrbonyl) hyrazide, teverelix (D-alaninamide,N-acetyl-3-(2-naphthalenyl) -D-alayl-4-chloro-pheuylalanyl-3-(3-pyridinyl) -D-alanyl-L-seryl-L-tyrosyl-N6-(aminocarbonyl)-D-lysyl-L-leucyl-N6-(1-methylethyl)-L-lysyl-L-prolyl, cetrorelix (D-Alaninamode, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl, ganirelix (N-Ac-D-Nal, D-pCl-Phe,D-Pal,DhArg(Et)2,hArg(Et)2,D-Ala) GnRH, alanex, abarelix (D-Alaninamide,N-acetyl-3-(2-naphthalenyl)-D-alanyl-4-chloro-D-phenylalanyl-3-(3-pyridinyl)-D-alanyl-L-seryl-N-methyl-L-tryosyl-D-asparainyl-L-leucyl-N6-(1-methylethyl)-L-lysyl-L-prolyl; N-(S)-tetrahydrofuroyl-Gly-D2Nal-D4Ciphe-D3Pal-Ser-NmeTyr-D-lys(Nic)-Leu-Lys(Isp)-Pro-D-Ala-NH2; isopropyl-13-(N-benzyl-N-methaminomethyl)-7-(2,6-diflurobenzyl)-4,7-dihydro-2-(4-isobutyrylaminophenyl)-4-oxothieno(2,3-b))pyridine-5-carboxyatehydrochloride). Other preferred GnRH antagonists are described in U.S. Pat. Nos. 5,110,904, 5,300,492, 5,807,983, 5,169,932, 5,296,468 and 5,502,035.

(3) Somatostatin Analogues

Particularly preferred somatostatin analogues include somatostatin-14, octreotide, lanreotide and angiopeptin cyclopeptides (U.S. Pat. No. 5,569,647).

Formulations according to the invention which include a somatostatin analogue as the at least one active agent may be used for treating, for example, hyperinsulinaemia and peptic ulcers.

(4) Lipid Lowering Agents

Particularly preferred lipid lowering agents include compounds which Inhibit HMG CoA reductase such as cerevastatin, mevastatin, simvastatin, pravastatin and lovastatin.

Formulations according to the invention which includes these agents may be used for treating, for example, hyperlipoproteineamia.

(5) Cyclosporins

Preferred cyclosporins include naturally occurring cyclosporins (e.g. as described by Dreyfuss et al., (1976) Europ. J. Appl. Microbiol. Vol. 3: 125–133), and analogues (e.g. as described by Wenger R. M. (1982), Chemistry of Cyclosporin A in "Cyclosporin "A", White D. G. G. ed., Amsterdam; Elsevier).

Formulations according to the invention which include a cyclosporin or cyclosporin analogue as the at least one active agent may be used, for example, as immunosuppressive agents for prophylaxis and treatment of organ rejection in allogenieic transplants.

(6) Angiotensin Converting Enzyme Inhibitors

Preferred ACE inhibitors include captopril, enalapril, trandolaprilate, perindoprilate, quinaprilate, fasidotril, omapatrilate and lisinopril.

Formulations according to the invention which include such agents may be used, for example, as antihypertensives.

(7) Calcitonins

Preferred calcitonins include human, salmon, and porcine calcitonin. Analogues of these polypeptides may also be suitable.

Formulations according to the invention which include calcitonin or calcitonin analogues may be used for treatment of, for example, hypercalcemia and for decreasing concentrations of phosphate in patients suffering from hyperparathyroidism, vitamin D intoxication, and osteolytic bone metastases.

(8) Substance P Antagonists

Preferred substance P antagonists include fragment 4–11 (i.e. Pro-Gln-Gln-Phe-Phe-Gly-Leu-Met-$NH_2$ and variant forms), fragment 5–11 (i.e. Gln-Gln-Phe-Phe-Gly-Leu-Met-$NH_2$ and variant forms), fragment 6–11 (i.e. Gln-Phe-Phe-Gly-Leu-Met-$NH_2$ and variant forms), fragment 7–11 (i.e. Phe-Phe-Gly-Leu-Met-$NH_2$), fragment 8–11 (i.e. Phe-Gly-Leu-Met-$NH_2$) and fragment 9–11 (i.e. Gly-Leu-Met-$NH_2$). Other suitable substance P antagonists include those described in the present applicant's co-pending Australian Provisional Patent Application No. PP9008.

Formulations according to the invention which include substance P antagonists may be used for treatment of cancer including chemotherapy-induced nausea and vomiting, pain, allergy, asthma, inflammatory conditions including inflammatory bowel disease and depression.

(9) Painkillers

Preferred painkillers include opioids such as morphine, levorphanol and meperidine (pethidine), and amide local anaesthetics such as bupivacaine, lidocaine, etidocaine and mepivacaine.

Formulations according to the invention which include such painkilling agents may be used to treat acute pain (e.g. such as that experienced by hip replacement patients) or chronic regional pain.

(10) Opioid Antagonists

Preferred opioid antagonists include naltrexone, naloxone and methadone.

Formulations according to the invention which include opioid antagonists may be used for treatment of opioid dependency.

(11) Anti-depressants

Preferred anti-depressants include venlafaxine, triflupromazine, methotrimeprazine, promethazine, buspirone, gepirone and fluoxetine (Prozac).

(12) Non-steroidal Anti-inflammatory Agents

Preferred non-steroidal anti-inflammatory agents include naproxen sodium indomethacin, sulindac, tolmelin, acemetacin, zomepirac, mefenamic acid, fenoprofen, flufenamic acid, phenylbutazone, flurbiprofen, ketoprofen and axsain.

Formulations according to the invention which include non-steroidal anti-inflammatory agents may be used for the treatment of post-operative inflammation and inflammation associated with, for example, rheumatoid arthritis.

(13) Miscellaneous

Other suitable active agents include paroxetine for treatment of social anxiety disorder/social phobia, galanin antagonists such as galanin fragment 1-13-Pro-Pro-Ala-Leu-Ala-Leu-Ala amide and galanin (1-13)-spantide 1 for treatment of obesity, eating disorders, depression and pain; activin and inhibin fragments such as α-subunit fragment 1-32 and β-fragment 67-94 for fertility control; adrenocorticotropic hormone (ACTH) and variants and fragments for treatment of West Syndrome and infantile spasms; growth hormone and its analogues for replacement therapy in growth-hormone deficient children; erythropoietin (EPO) and its analogues for treatment of anaemia; endothelin antagonists for prevention of congestive heart failure, prevention of acute renal failure and subarachnoid haemorrhage, prevention and treatment of atherosclerosis, treatment of hypertension, prevention of stroke and treatment of chronic obstructive pulmonary disease; leptin and its agonists and antagonists for treatment of obesity and eating disorders such as anorexia nervosa, and for weight loss; thyrotropin releasing hormone (TRH) and its analogues (e.g. pGlu-His-Pro-Gly) for treatment of, for example, epilepsy; and theophylline and its analogues for the treatment of asthma, systemic capillary leak syndrome and Parkinson's disease. Vaccine antigens, including DNA encoding vaccine antigens, may also be delivered in a formulation according to the present invention.

Formulations according to the invention may include a combination of active agents. Examples of preferred combinations (comprising "Agent 1" and "Agent 2") are shown in Table 1.

TABLE 1

| Agent 1 | Agent 2 |
| --- | --- |
| HMG Co A reductase inhibitor | Gemfibrozil |
| Non-steroidal anti-inflammatory agent | Mycophenolate mofelil |
| GnRH agonist | Trk tyrosine inhibitor |
| GnRH agonist | Testosterone |
| Calcitonin | Estrogen |
| Calcitonin | Etridonate |
| Calcitonin | Pamridonate |
| Octreotide | α-interferon |
| Octreotide | IGF-1 |
| Octreotide | Miclodrine |
| GnRH agonist | Flutamide |
| Etofylline | Theophylline |

Preferably, the at least one active agent is/are of low to moderate lipophilicity. More preferably, at least one active agent has a log octanol/water partition coefficient (log P) (Ruelle and Kesselring (1998), J Pharm Sci. Vol. 87:1115–24) in the range of 5.0 to –3.0. Most preferred are active agents having a log P value in the range of 3.0 to –3.0 and, particularly, those having a log P value in the range of 1.0 to –3.0.

Log P values for representatives of the abovementioned classes of active agents are provided in Table 2.

TABLE 2

| Agent | log octanol/water partition (log P) |
| --- | --- |
| octreotide | 1.40 |
| cyclosporin A | 2.90 |
| captopril | –1.86 |
| trandolaprilate | 1.02 |
| perindoprilate | –0.36 |
| quinaprilate | 0.69 |
| morphine | 0.76 |
| lidocaine | 2.26 |
| methadone | 3.93 |
| promethazine | 4.75 |
| indomethacin | 4.27 |
| flufenamic acid | 1.14 |
| phenylbutazone | 3.16 |
| theophylline | –0.02 |
| etofylline | 0.35 |
| TRH | <2.40 |

The pore-forming agent may be any agent or combination of agents which enables the sustained release of the at least one active agent from the stearin excipient, with the proviso that when the at least one active agent is a GnRH agonist(s) the pore-forming agent is not lecithin.

Preferably, the pore-forming agent or agents is/are selected from water-soluble agents such as inorganic salts (e.g. chlorides, phosphates and sulphates), organic salts (e.g. acetates, formates, propionates, glutamates, and aspartates), sugars (e.g. glucose, trehalose, mannose, galactose, sucrose and low molecular weight carbohydrates such as hydroxy propyl methylcellulose (HPMC) and carboxy methylcellulose (CMC)), aminosugars (e.g. glucosamine and galactosamine), amino acids/peptides (e.g. lysine, arginine, glutamic acid, aspartic acid, carnosine and aspartame), water-soluble proteins and water-soluble vitamins (e.g. Vitamin B).

Presently, the most preferred pore-forming agent is lecithin (except where the at least one active agent is a GnRH agonist(s)) and the amino acid lysine. Lecithin is a mixture of diglycerides of stearic, palmitic and oleic acids linked to the choline ester of phosphoric acid. The efficacy of lecithin as a pore-forming agent in a sustained release formulation comprising deslorelin and stearin is described in International patent application No. PCT/AU96/00370 (WO 97/00093), the entire disclosure of which is incorporated herein by reference.

As will be evident from the examples herein, variation of the identity and/or amount of the pore-forming agent(s) utilised allows for the manipulation of the release profile of the active agent(s) to suit particular therapeutic uses.

The stearin excipient is preferably in a non-crystalline form. Stearin is partially hydrogenated palm oil having, as the principle fatty acids, C16:0(45%) and C18:0(53%). The melting point of stearin is about 60° C. It is believed that the use of stearin as the excipient contributes to the success of the formulations according to the invention, because it appears, surprisingly, to produce only a minimal to mild inflammatory response in a recipient resulting in the encapsulation of the formulation within a thin layer of fibroblasts. It will be appreciated by persons skilled in the art, that alternative formulations comprising excipient(s) with similar characteristics to those included in the formulation defined above in the first aspect may likewise provoke minimal to mild inflammatory responses and consequently be useful for the sustained-release of an active agent(s). Such alternative formulations are to be regarded as falling within the scope of the present invention.

The formulations according to the invention may be for administration to humans and other animals selected from dogs, cats, other domestic animals, and captive wildlife.

Typically, the formulations will release the active agent(s), in vitro, into phosphate buffered saline (PBS: pH 7.3, prepared by dissolving 8.00 g of sodium chloride, 1.00 g di-sodium hydrogen phosphate anhydrous, 0.40 g sodium dihydrogen phosphate dihydrate (0.31 g if anhydrous), and 0.05 g sodium azide in 1 litre of deionised water), at 37° C. at a rate of about 2–350 μg/day for at least 7 days and up to about 2 years.

Further, the formulations will typically exist as a depot formulation for example in the form of free flowing beads or rods which may have been extruded.

Extruded rods may be cut into predetermined lengths for implantation, by standard techniques, in a human or other animal. As will be readily appreciated, the length of the rod will determine the rate and dose of the active agent(s). As opposed to implanting longer rods more than one rod can be implanted in each human or other animal. Injection of a suspension of formulated particulate material such as free flowing beads may also deliver the active agent(s) at the desired rate and dose.

Formulations for administration as free flowing beads and/or implants, particularly to dogs, may be produced as follows:

Stearin (supplied as free flowing beads of 1 mm or less in diameter made by Vandenberg Foods) and pore-forming agent are mixed. The active agent may then be added and thoroughly mixed into the excipient and pore-forming agent mixture. This material may then be used for injection. Alternatively the mixture can be transferred to the barrel of a ram extruder that has a 1 mm nozzle attached and is equilibrated to 55° C. (or other temperature sufficient to soften the stearin). After attaching the ram, pressure (40 psi) is applied until the product begins to extrude. At this point the pressure can be backed off and the product allowed to reach 55° C. (or other temperature sufficient to soften the stearin). The product may then be extruded at, for example, a rate of 3 g over a 30 second period. The resulting extrudate is then allowed to cool and then broken up and re-extruded through a 1 mm nozzle to ensure uniformity of content throughout the mix. The 1 mm nozzle may then be replaced with a 2.3 mm diameter nozzle and the product extruded (using the same temperature equilibration procedure prior to extrusion). After cooling the long rods produced can be sectioned into lengths of the required weight and the sectioned lengths sterilised by gamma-irradiation.

Alternatively, formulations for administration as bioimplants, particularly for dogs, may be produced by:

Stearin and pore-forming agent are mixed. The active agent may then be added and thoroughly mixed into the excipient and pore-forming agent mixture. The mixture can then be transferred to the barrel of an extruder that has a 2.3 mm nozzle attached and which has been equilibrated to a temperature sufficient to soften the stearin. The extruder is started and the product begins to extrude and the extrudate is cut to length. The sectioned length can be terminally sterilised.

Further, in preparing formulations according to the present invention, especially where the at least one active agent is a peptide(s), polypeptide(s) or protein(s), it is preferred that the at least one active agent is firstly pre-treated with a process comprising at least two freeze drying steps. Such freeze drying steps may be conducted in accordance with any of the commonly known methods for freeze drying of proteinaceous materials. It is, however, preferred that the active agent(s) be freeze dried from a 5–50% (more preferably, 5–15%) (w/w) solution of the active agent(s) in a suitable solvent (e.g. an alcohol solution such as 30% (w/w) ethanol in water). The freeze dried active agent(s) may then be redissolved or homogenised in a suitable solvent (e.g. 25–75% (w/w) in a diluted weak acid solution such as 1–5% (w/w) acetic acid in water) and subsequently freeze dried again. Thus, the freeze drying of the active agent(s) may comprise the steps of;

(i) forming a 5–50% (w/w) solution of the active agent(s),
(ii) freeze drying said solution of step (i),
(iii) forming a 25–75% (w/w) solution or homogenate from said freeze dried active agent(s), and
(iv) freeze drying said solution or homogenate of step (iii).

The term "on an active basis" is to be given its usual meaning in the art That is, it is used to indicate that the % amount (w/w) of peptide agonist or analogue present in a formulation is based on the dry weight of the peptide agonist or analogue.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by reference to the following, non-limiting examples and accompanying figures.

BRIEF DESCRIPTION OF THE ACCOMPANYING FIGURES

FIG. 1 provides a graph showing average daily in vitro release profiles from three 100 mg rods of each of formulations:

(I) 6% deslorelin, 2% lysine and balance stearin; and
(II) 6% deslorelin, 5% lysine and balance stearin.

The graph demonstrates an initial rapid release of the active agent and then continued release extending over a prolonged period (110 days).

Figure 2:
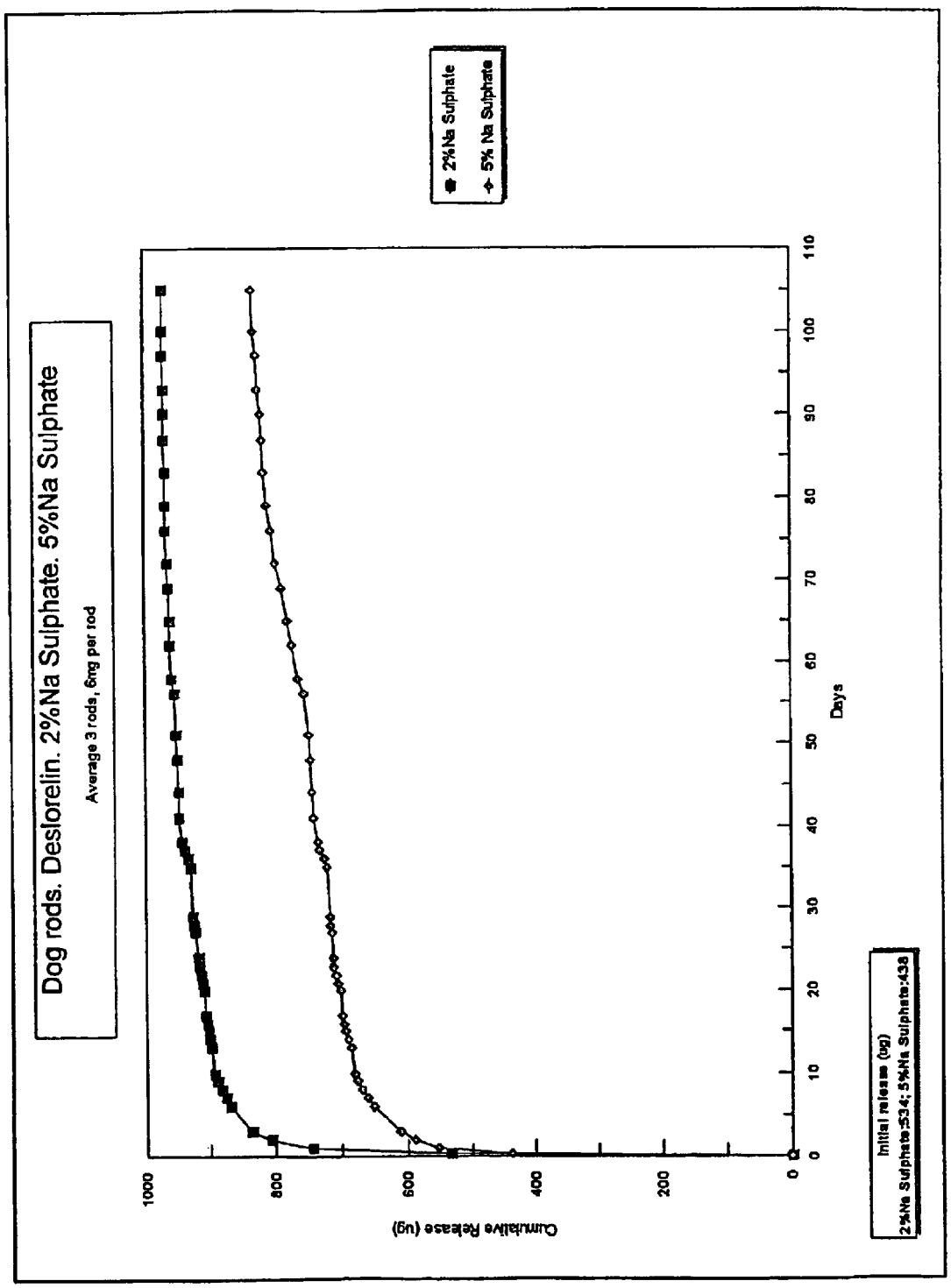

FIG. 2 provides a graph showing the average daily in vitro release profile from the 100 mg rods of each of formulations:

(III) 6% deslorelin, 2% sodium sulphate and balance stearin; and
(IV) 6% deslorelin, 5% sodium sulphate and balance stearin.

The graph demonstrates that a greater initial rapid release of deslorelin (534 $\mu$g vs. 438 $\mu$g) was achieved using 5% sodium sulphate as the pore-forming agent. After the initial rapid release (finished at about day 10), the rate of release was about 10–2 $\mu$g/day for the next 95 days for both formulations.

Figure 3:
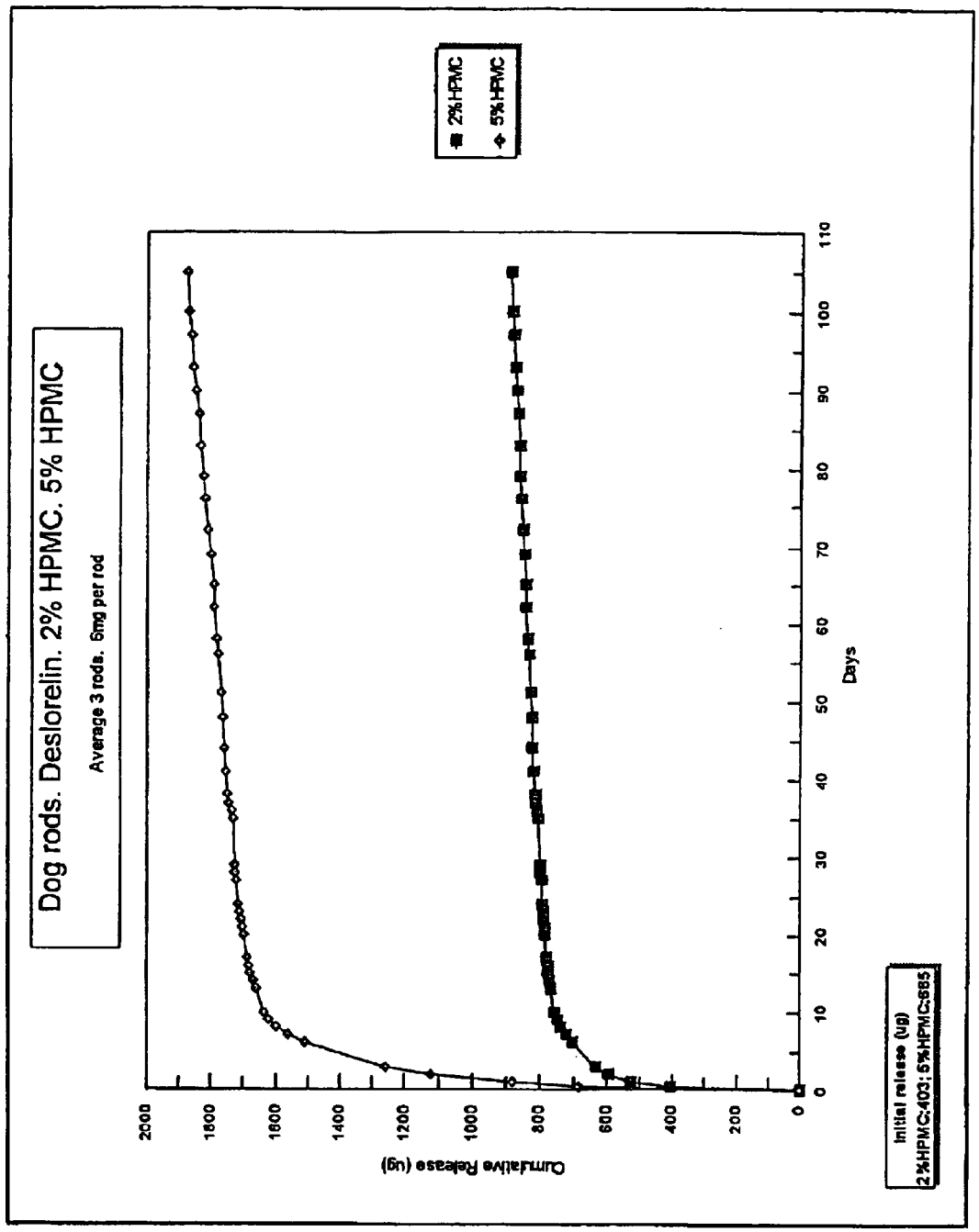

FIG. 3 provides a graph showing the average daily in vitro release profile from three 100 mg rods of each of formulations:

(V) 6% deslorelin, 2% hydroxy propyl methylcellulose (HPMC) and balance stearin; and
(VI) 6% deslorelin, 5% hydroxy propyl methylcellulose (HPMC) and balance stearin.

The graph demonstrates that a much greater initial rapid release of deslorelin (685 $\mu$g vs. 403 $\mu$g) was achieved using 5% HPMC as the pore-forming agent. After the initial rapid release (finished at about day 10), the rate of release was about 10–2 $\mu$g/day for the next 95 days for both formulations.

Figure 4:
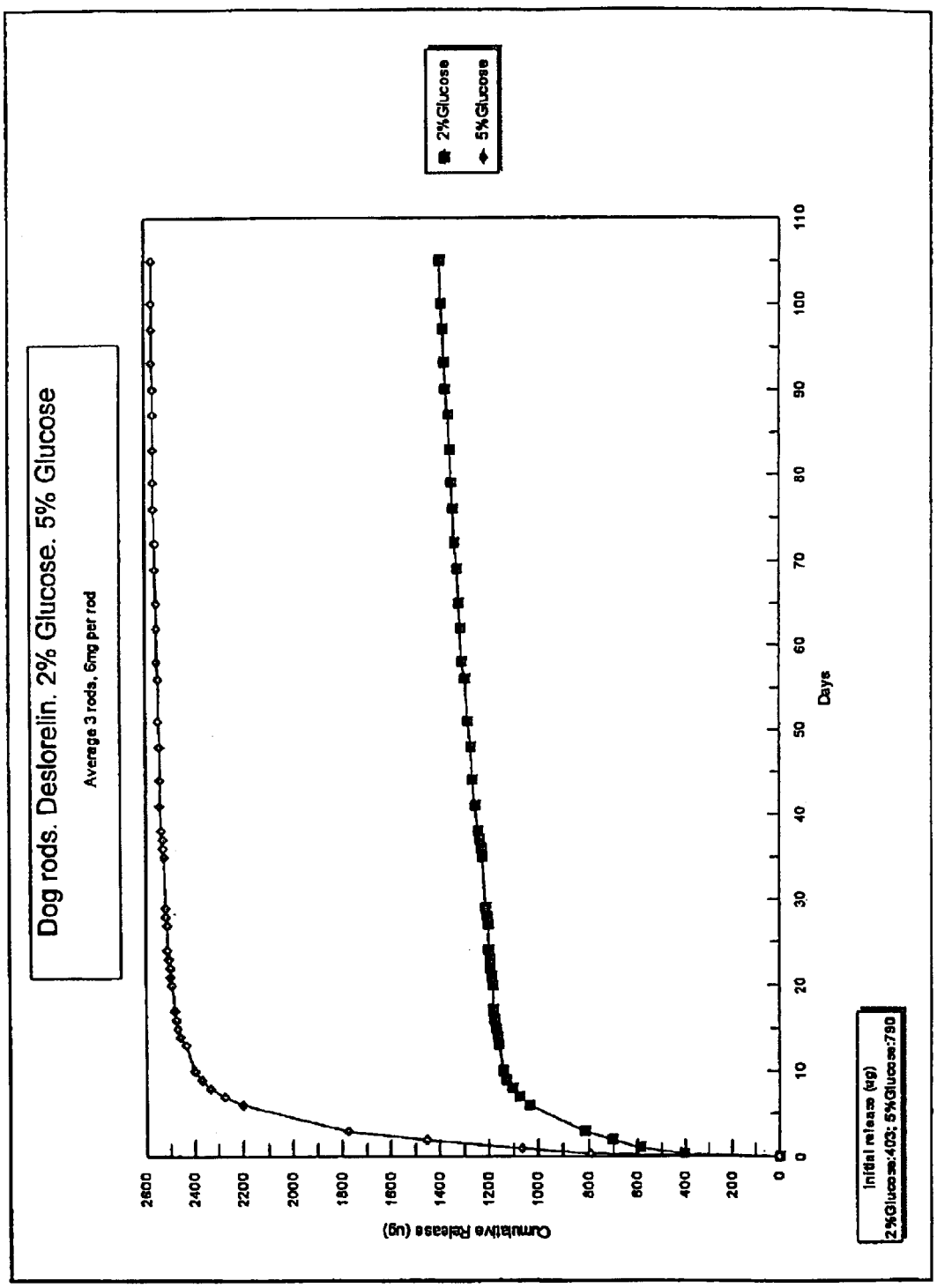

FIG. 4 provides a graph showing the average daily in vitro release profile from three 100 mg rods of each of formulations:

(VII) 6% desloreline, 2% glucose and balance stearin; and
(VIII) 6% deslorelin, 5% glucose and balance stearin.

The graph demonstrates that a much greater initial rapid release of deslorelin (790 $\mu$g vs. 403 $\mu$g) was achieved using 5% glucose as the pore-forming agent. After the initial rapid release (finished at about day 10), the rate of release was about 50–2 $\mu$g/day for the next 95 days for both formulations.

Figure 5:
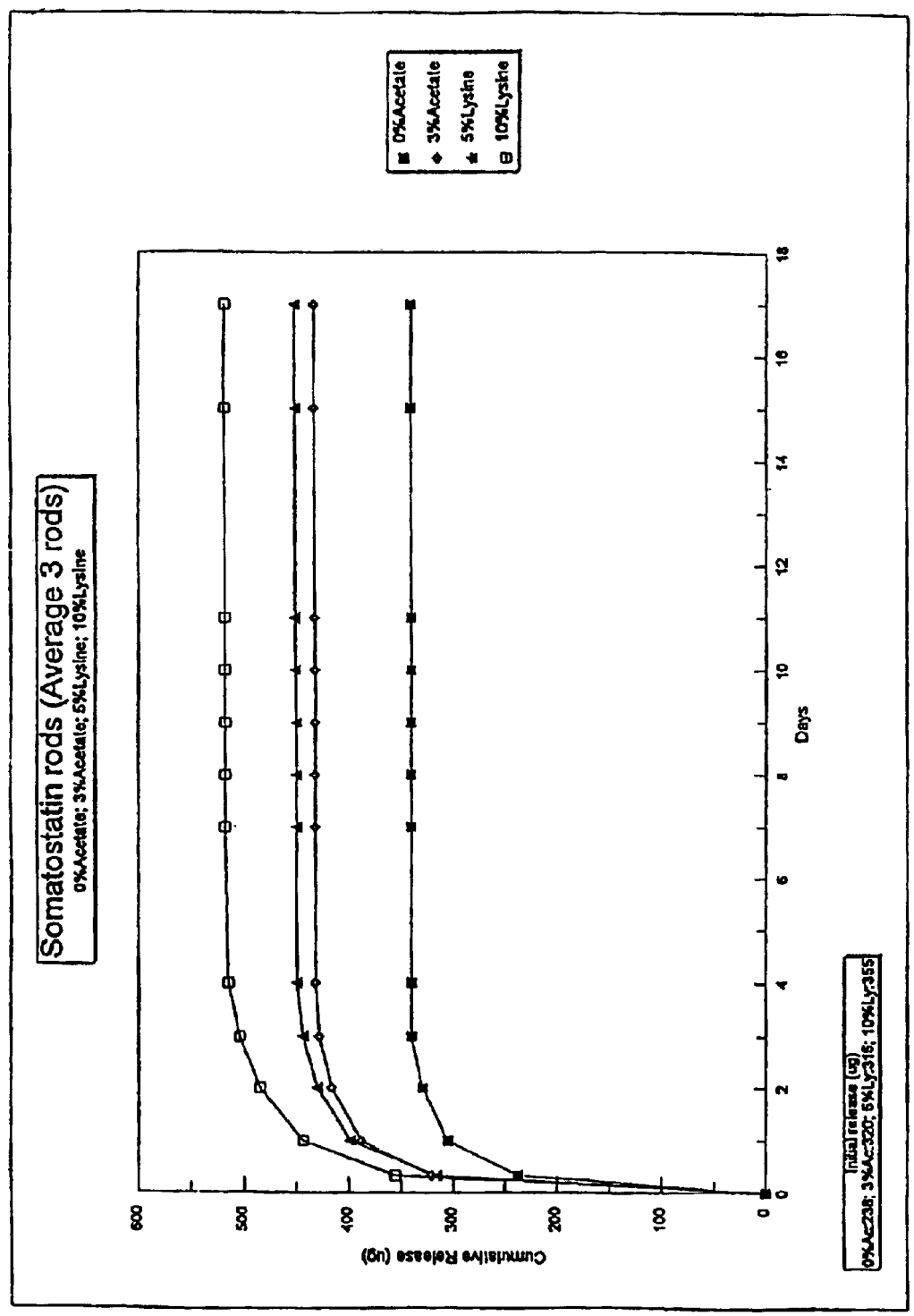

FIG. 5 provides a graph showing the average daily in vitro release profile from three 100 mg rods of each of formulations:

(IX) 6% somatostatin, 0% acetate and balance stearin;
(X) 6% somatostatin, 3% acetate and balance stearin;
(XI) 6% somatostatin, 5% lysine and balance stearin; and
(XII) 6% somatostatin, 10% lysine and balance stearin.

The graph demonstrates that a greater initial rapid release of somatostatin was achieved using lysine than sodium acetate as the pore-forming agent. After the initial rapid release (finished at about day 2), the rate of release in all cases slowed and plateaued by day 7.

Figure 6:
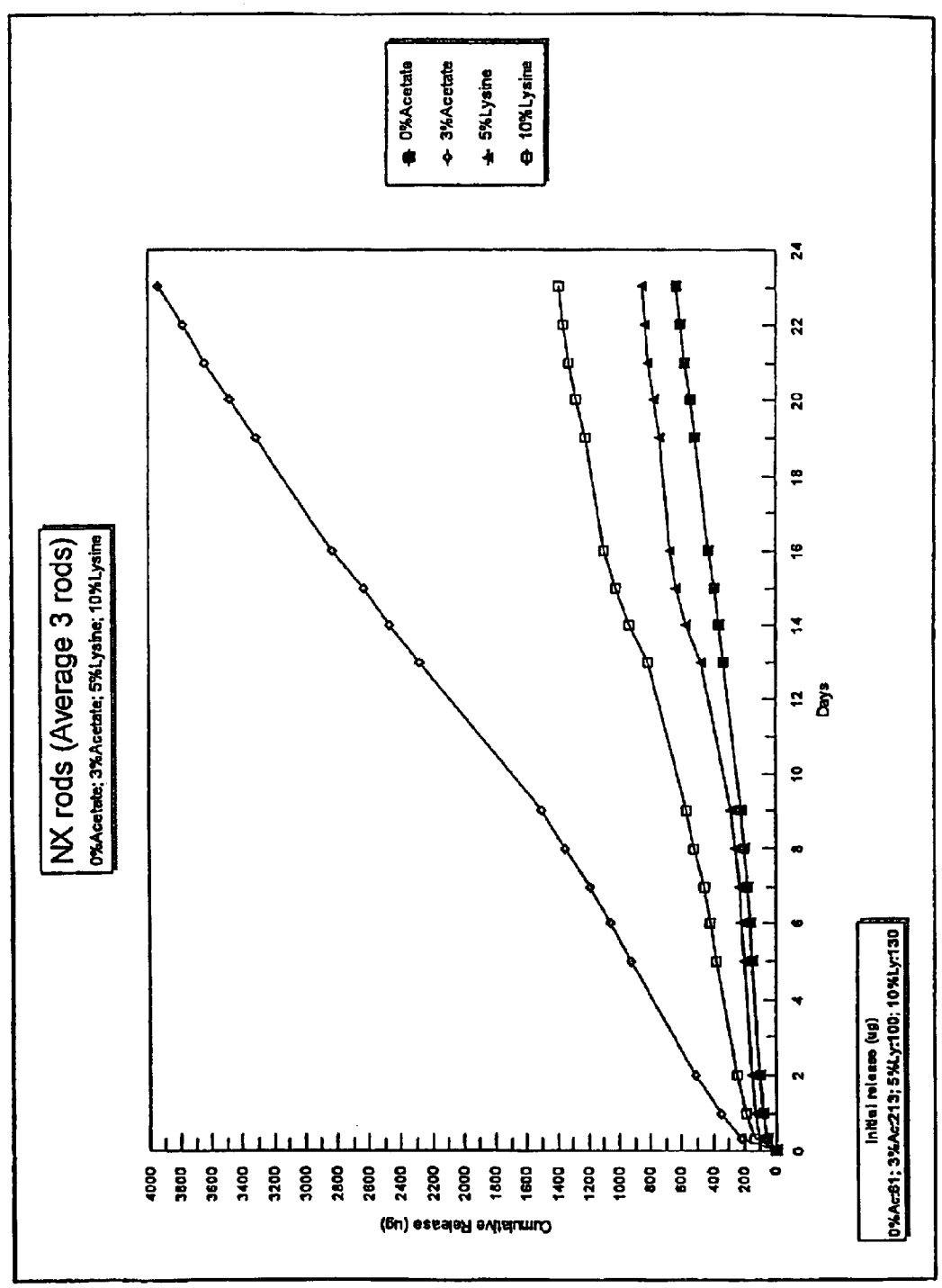

FIG. 6 provides a graph showing the average daily in vitro release profile from three 100 log rods of each of formulations:

(XVII) 6% naltrexone (NX), 0% pore forming agent and balance stearin;
(XIV) 6% naltrexone (NX), 3% acetate and balance stearin;
(XV) 6% naltrexone (NX), 5% lysine and balance stearin; and
(XVI) 6% naltrexone (NX), 10% lysine and balance stearin.
The graph demonstrates that a sustained gradual release of naltrexone was achieved by all formulations over 23 days of testing, although the average daily release was low when no pore-forming agent was included.

Figure 7:
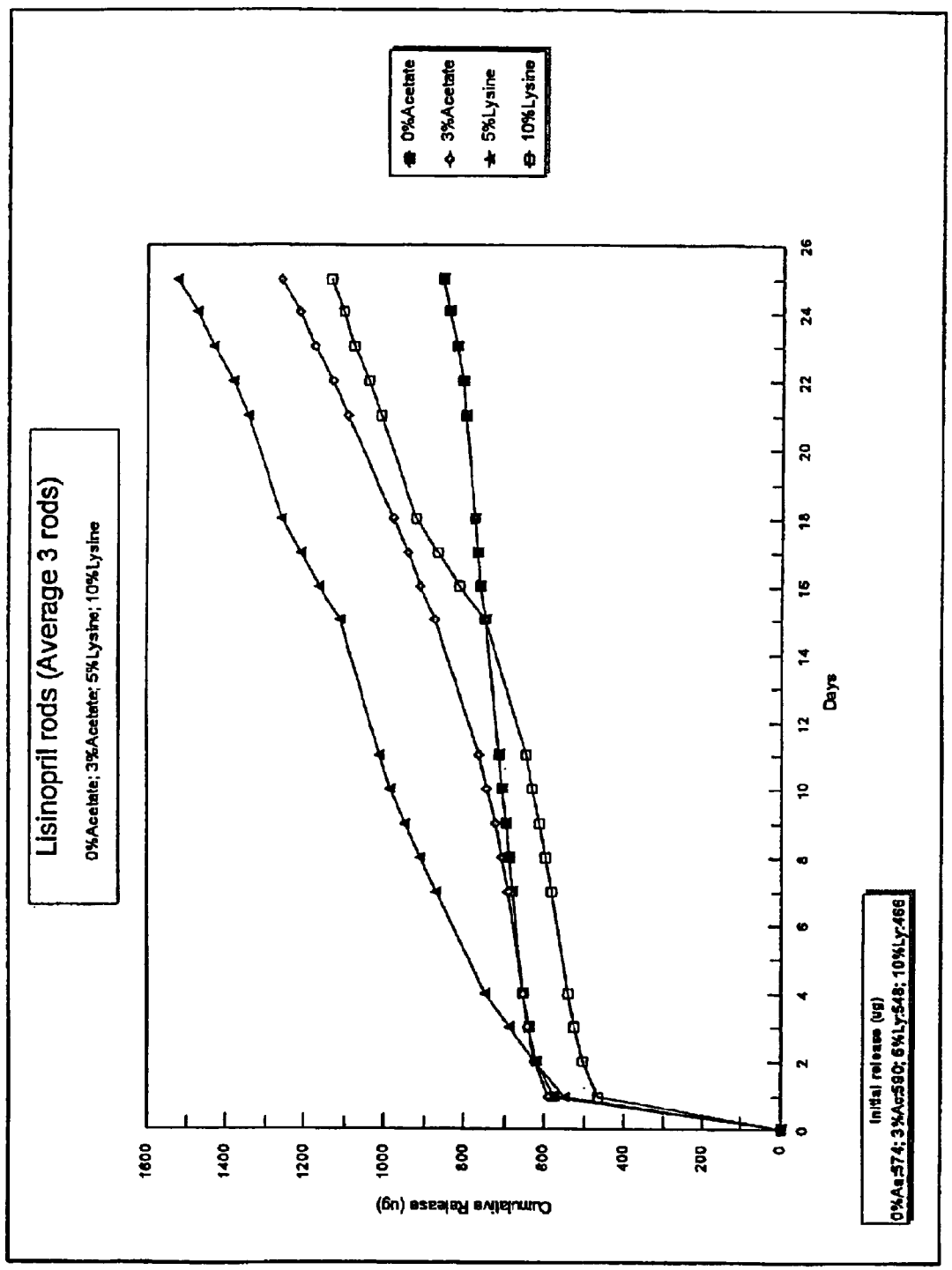

FIG. 7 provides a graph showing the average daily in vitro release profile from three 100 mg rods of each of formulations:
(XVII) 6% lisinopril, 0% sodium acetate and balance stearin;
(XVIII) 6% lisinopril. 3% sodium acetate and balance stearin;
(XIX) 6% lisinopril, 5% lysine and balance stearin; and
(XX) 6% lisinopril, 10% lysine and balance stearin.
The graph demonstrates that following an initial rapid release (finished at about day 1) a sustained gradual release of lisinopril was achieved by all formulations over 25 days of testing, although the average daily release of this period of sustained release was low in the case of formulation XVII (i.e. 0% pore-forming agent).

Figure 8:
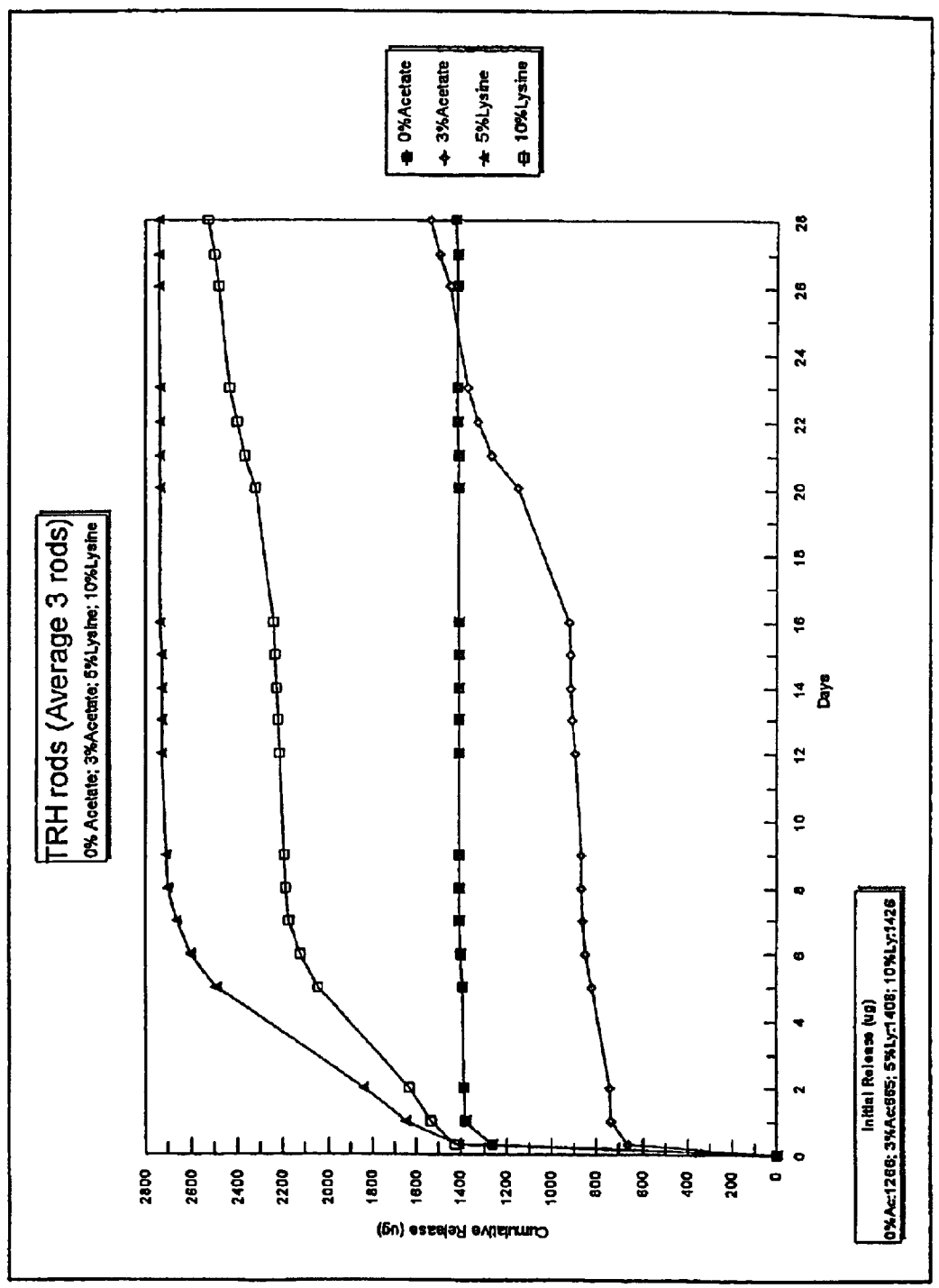

FIG. 8 provides a graph showing the average daily in vitro release profile from three 100 mg rods of each of formulations:
(XXI) 6% thyrotropin releasing hormone (TRH), 0% acetate and balance stearin;
(XXII) 6% thyrotropin releasing hormone (TRH), 3% acetate and balance stearin;
(XXIII) 6% thyrotropin releasing hormone (TRH), 5% lysine and balance stearin; and
(XXHV) 6% thyrotropin releasing hormone (TRH), 10% lysine and balance stearin.
The graph demonstrates that following a very rapid initial release, a sustained gradual release of TRH was achieved with formulations XXII, XXIII and XXIV over the 28 day period of of testing. Where no pore-forming agent was included, no further TRH release was observed after day 1.

Figure 9:
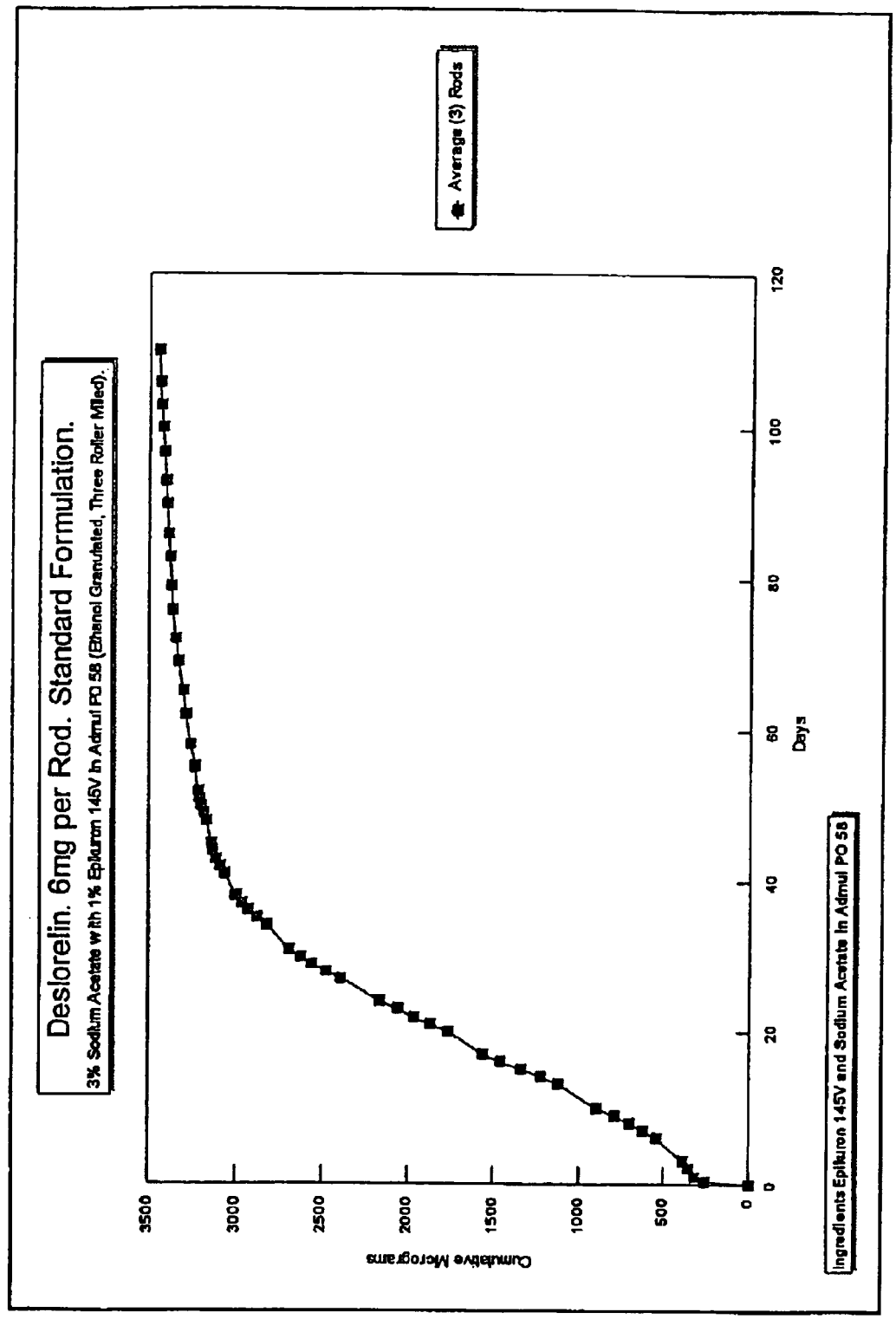

FIG. 9 provides a graph showing the average daily in vitro release profile from three 100 mg rods of formulation:
(XXV) 6% deslorelin, 3% sodium acetate and balance stearin.
The graph demonstrates that sustained release of deslorelin over 110 days was achieved.

EXAMPLE

Formulations Comprising Deslorelin and Lysine

Formulations I and II (detailed above) were prepared as follows:

Stearin (supplied as free flowing beads of 1 mm or less in diameter made by Quest International Pty Ltd (Netherlands) and lysine (supplied as a deep brown viscous syrup from Lucas Myer (Germany) were hand mixed using a spatula in a small beaker. Deslorelin (Bachem, Switzerland) pretreated by the above described freeze drying process, was then added and thoroughly mixed into the excipients. The mixed material was transferred to the barrel of a ram extruder that has a 1 mm nozzle attached and is equilibrated to 55° C. The ram extrusion pressure was 40 psi. The ram was attached and pressure applied until the product began to extrude. At this point the pressure was backed off and the product allowed to reach 55° C. The product was then extruded at a rate of 3 g over a 30 second period. The resulting exudate was allowed to cool and then broken up and re-extruded through a 1 mm nozzle. This step was included to ensure uniformity of content throughout the matrix. The 1 mm nozzle was then replaced with a 2.3 mm diameter nozzle. The same product temperature equilibration procedure was conducted prior to extrusion. The product was then extruded and after cooling the long rods produced were sectioned into lengths of the required weight.

FIG. 1 provides results of in vitro deslorelin release with 100 mg rods containing 6 mg deslorelin. The assay involved immersing each rod into separate containers with 1 ml of phosphate buffered saline (PBS; as hereinbefore described) placed in a reciprocating water bath at 37° C. The PBS was replaced daily and the withdrawn PBS assayed for deslorelin with HPLC. The figure shows that after an initial rapid release of deslorelin, sustained release extending over a prolonged period (110 days) was achieved. The average daily rate of deslorelin release during the sustained release period was within the range 50–2 µg/day.

Formulations Comprising Deslorelin and Sodium Sulphate

Formulations III and IV were prepared with sodium sulphate (Ajax Chemicals, USA) as the pore-forming agent in the same manner as described above for deslorelin/lysine formulations.

FIG. 2 provides results of in vitro deslorelin release with 100 mg rods containing 6 mg deslorelin. The figure shows that a greater initial rapid release of deslorelin (534 µg vs. 438 µg) was achieved using a 5% concentration of sodium sulphate rather than a 2% concentration. After the initial rapid release (finished at about day 10), the rate of release was about 10–2 µg/day for the next 95 days for both formulations.

Formulations Comprising Deslorelin and HPMC

Formulations V and VI were prepared with hydroxy propyl methylcellulose (HPMC) as the performing agent in the same manner as described above for deslorelin/lysine formulations.

FIG. 3 provides results of in vitro deslorelin release with 100 mg rods containing 6 mg desloelin. The figure shows that a much greater initial rapid release of deslorelin (685 µg vs. 403 µg) was achieved using 5% HPMC rather than 2% HPMC. After the initial rapid release (finished at about day 10%), the rate of release was about 10–2 µg/day for the next 95 days for both formulations.

Formulations Comprising Deslorelin and Glucose

Formulations VII and VIII were prepared with glucose (Ajax Chemicals, USA) as the pore-forming agent in the same manner as described above for deslorelin/lysine formulations.

FIG. 4 provides results of in vitro deslorelin release with 100 mg rods, containing 6 mg deslorelin. The figure shows that a much greater initial rapid release of deslorelin (790 µg vs. 403 µg) was achieved using 5% glucose rather than 2% glucose as the pore-forming agent. After the initial rapid release (finished at about day 10), the rate of release was about 50–2 µg/day for the next 95 days for both formulations.

Formulations Comprising Somatostatin and Sodium Acetate or Lysine

Formulations IX to XII were prepared with sodium acetate or lysine as the pore-forming agent in a manner similar to that described above for deslorelin/lysine formulations. The somatostatin was obtained from Bachem (Switzerland).

FIG. 5 provides results of in vitro somatostatin release with 100 mg rods, containing 6 mg somatostatin. The figure shows that a greater initial rapid release of somatostatin was achieved using lysine than sodium acetate as the pore-forming agent.

Formulations Comprising Naltrexone and Sodium Acetate or Lysine

Formulations XIII to XVI were prepared with sodium acetate or lysine as the pore-forming agent in a manner similar to that described above for deslorelin/lysine formulations.

FIG. 6 provides results of in vitro naltrexone release with 100 mg rods, containing 6 mg deslorelin. The figure shows that a sustained gradual release of naltrexone was achieved by all formulations over 23 days of testing, although the average daily release was low when no pore-forming agent was included.

Formulations Comprising Lisinopril and Sodium Acetate or Lysine

Formulations XVII to XX were prepared with sodium acetate or lysine as the pore-forming agent in a manner similar to that described above for deslorelin/lysine formulations. The lisinopril was obtained from Sigma Chemical Co. (USA).

FIG. 7 provides results of in vitro lisinopril release from 100 mg rods, containing 6 mg lisinopril. The figure shows that following an initial rapid release (finished at about day 1) a sustained gradual release of lisinopril was achieved by all formulations over 25 days of testing, although the average daily release of this period of sustained release was low in the case of formulation XVII which contains no pore-forming agent.

Formulations Comprising TRH and Sodium Acetate or Lysine

Formulations XXH to XXIV were prepared with sodium acetate or lysine as the pore-forming agent in a manner similar to that described above for deslorelin/lysine formulations. The TRH was obtained from Sigma Chemical Co (USA).

FIG. 8 provides results of in vitro TRH release from 100 mg rods, containing 6 mg TRH. The figure shows that following a very rapid initial release, a sustained gradual release of TRH was achieved with formulations XXII, XXIII and XXIV over the 28 day period of of testing. Where no pore-forming agent was included, no further TRH release was observed after day 1.

Formulations Comprising Deslorelin and Sodium Acetate

Formulation XXV were prepared with sodium acetate as the pore-forming agent in the same manner as described above for deslorelin/lysine formulations.

FIG. 9 provides results of in vitro deslorelin release with 6 mg rods. The figure shows that sustained release of deslorelin over 110 days was achieved.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A pharmaceutical and/or veterinary formulation comprising about 2–30% (w/w) (on an active basis) of at least one active agent, about 0.5–20.0% (w/w) of a pore-forming agent and the balance stearin, with the proviso that where the at least one active agent is a gonadotropin-releasing hormone(GnRH) agonist(s) the pore-forming agent is not lecithin.

2. A formulation according to claim 1, wherein the formulation comprises about 5–10% (w/w) (on an active basis) of at least one active agent, about 1.0–10.0% (w/w) of a pore-forming agent and the balance stearin.

3. A formulation according to claim 1, wherein the formulation comprises about 5–10% (w/w) (on an active basis) of at least one active agent, about 2.0–5.0% (w/w) of a pore-forming agent and the balance stearin.

4. A formulation according to claim 1, wherein the at least one active agent is selected from peptides, polypeptides, proteins and nucleic acid compounds and derivatives.

5. A formulation according to claim 1, wherein the at least one active agent is selected from GnRH agonists.

6. A formulation according to claim 5, wherein the GnRH agonist(s) is selected from deslorelin, eulexin, goserelin, leuprolide, dioxalan derivatives, triptorelin, meterelin, buserelin, histrelin, nafarelin, lutrelin, leuprorelin and LHRH analogues.

7. A formulation according to claim 1, wherein the at least one active agent is selected from GnRH antagonists.

8. A formulation according to claim 7, wherein the GnRH anatgonist is selected from ramorelix, teverelix, cetrorelix, ganirelix, alanex and abarelix.

9. A formulation according to claim 1, wherein the at least one active agent is selected from somatostatin analogues.

10. A formulation according to claim 9, wherein the somatostatin analogue is selected from somatostatin-14, octreotide, laureotide and angiopeptin cyclopeptides.

11. A formulation according to claim 1, wherein the at least one active agent is selected from lipid lowering agents.

12. A formulation according to claim 11, wherein the lipid lowering agent is selected from cerevastatin, mevastatin, simvastatin, pravastatin and lovastatin.

13. A formulation according to claim 1, wherein the at least one active agent is selected from cyclosporins and cyclosporin analogues.

14. A formulation according to claim 13, wherein the cyclosporin or cyclosporin analogue is cyclosporin A.

15. A formulation according to claim 1, wherein the at least one active agent is selected from angiotensin converting enzyme inhibitors.

16. A formulation according to claim 15, wherein the angiotensin converting enzyme inhibitor is selected from captopril, enalapril, trandolaprilate, perindoprilate, quinaprilate, fasidotril, omapatrilate and lisinopril.

17. A formulation according to claim 1, wherein the at least one active agent is selected from calcitonins and calcitonin analogues.

18. A formulation according to claim 17, wherein the calcitonin is selected from human calcitonin, salmon calcitonin and porcine calcitonin.

19. A formulation according to claim 1, wherein the at least one active agent is selected from substance P antagonists.

20. A formulation according to claim 19, wherein the substance P antagonist is selected from Pro-Gln-Gln-Phe- Phe-Gly-Leu-Met-NH$_2$, Gln-Gln-Phe-Phe-Gly-Leu-Met-NH$_2$, Gln-Phe-Phe-Gly-Lou-Met-NH$_2$. Phe-Phe-Gly-Leu-Met-NH$_2$, Phe-Gly-Leu-Met-NH$_2$ and Gly-Leu-Met-NH$_2$.

21. A formulation according to claim 1, wherein the at least one active agent is selected from pain killing agents.

22. A formulation according to claim 21, wherein the painkilling agent is selected from morphine, levorphanol, meperidine, bupivacaine, lidocaine, etidocaine and mepivacaine.

23. A formulation according to claim 1, wherein the at least one active agent is selected from opioid antagonists.

24. A formulation according to claim 23, wherein the opioid antagonist is selected from naltrexone, naloxone and methadone.

25. A formulation according to claim 1, wherein the at least one active agent is selected from anti-depressant agents.

26. A formulation according to claim 25, wherein the anti-depressant agent is selected from venlafaxine, triflupromazine, methotrimeprazine, promethazine, buspirone, gepirone and fluoxetine.

27. A formulation according to claim 1, wherein the at least one active agent is selected from non-steroidal anti-inflammatory agents.

28. A formulation according to claim 27, wherein the at least one active agent is naproxen sodium indomethacin, sulindac, tolmelin, acemetacin, zomepirac, mefenamic acid, fenoprofen, flufenamic acid, phenylbutazone, flurbiprofen, ketoprofen and axsain.

29. A formulation according to claim 1, wherein the at least one active agent is selected from paroxetine, galanin antagonists, activin, inhibin fragments, adrenocorticotropic hormone (ACTH) and variants and fragments thereof, growth hormone and growth hormone analogues, erythropoietin (EPO) and erythropoietin analogues, endothelin antagonists, leptin and leptin analogues, thyrotropin releasing hormone (TRH) and TRH analogues, theophylline and theophylline analogues.

30. A formulation according to claim 1, wherein the at least one active agent is selected from vaccine antigens and DNA encoding vaccine antigens.

31. A formulation according to claim 1, wherein the at least one active agent has a log octanol/water partition coefficient (log P) in the range of 5.0 to −3.0.

32. A formulation according to claim 31, wherein the at least one active agent has a log octanol/water partition coefficient (log P) in the range of 3.0 to −3.0.

33. A formulation according to claim 31, wherein the at least one active agent has a log octanol/water partition coefficient (log P) in the range 1.0 to −3.0.

34. A formulation according to claim 1, wherein the pore-forming agent is selected from inorganic salts, organic salts, sugars, amino sugars, amino acids, peptides, water-soluble proteins, water-soluble vitamins and combinations thereof.

35. A formulation according to claim 34, wherein the pore-forming agent is selected from lecithin, lysine, sodium sulphate, sodium acetate, glucose and hydroxy propyl methylcellulose (HPMC).

36. A formulation according to claim 1, wherein at least one active agent, is released in vitro into phosphate buffered saline, as herein before described, at 37° C. at a rate of about 2 ug–1.5 mg/day for at least 7 days.

37. A formulation according to claim 1, wherein the formulation is in the form of free flowing beads or rods.

38. A formulation according to claim 1, wherein the at least one active agent has been pre-treated with a process comprising at least two freeze drying steps.

39. A formulation according to claim 38, wherein the pre-treatment process comprises the steps of;

(i) forming a 5–50% (w/w) solution of the active agent(s), (ii) freeze drying said solution of step (i), (iii) forming a 25–75% (w/w) solution or homogenate from said freeze dried active agent(s), and (iv) freeze drying said solution or homogenate of step (iii).

40. A method of treating a disease or condition is a human or other animal, the method comprising administering to the human or other animal a formulation according to claim 1.

* * * * *